United States Patent [19]

Woodmansee

[11] Patent Number: 4,862,748
[45] Date of Patent: Sep. 5, 1989

[54] MULTIPLE ULTRASONIC TRANSDUCER WITH REMOTE SELECTOR

[75] Inventor: Wayne E. Woodmansee, Seattle, Wash.

[73] Assignee: The Boeing Company, Seattle, Wash.

[21] Appl. No.: 221,824

[22] Filed: Jul. 20, 1988

[51] Int. Cl.⁴ .............................................. G01N 29/04
[52] U.S. Cl. ........................................ 73/641; 73/644; 73/633
[58] Field of Search ................ 73/598, 600, 601, 628, 73/623, 633, 641, 644

[56] References Cited

U.S. PATENT DOCUMENTS

| | | | |
|---|---|---|---|
| 3,028,752 | 6/1959 | Bacon | 73/623 |
| 3,121,324 | 2/1964 | Cowan | 73/623 |
| 4,143,554 | 3/1979 | Nagy et al. | 73/641 |
| 4,185,501 | 1/1980 | Proudian et al. | 73/641 |
| 4,212,207 | 7/1980 | Conradi | 73/623 |
| 4,315,435 | 2/1982 | Proudian | 73/628 |
| 4,361,044 | 11/1982 | Kupperman et al. | 73/623 |
| 4,552,021 | 11/1985 | Miwa et al. | 73/644 |
| 4,757,821 | 7/1988 | Snyder | 73/623 |

Primary Examiner—Stewart J. Levy
Assistant Examiner—Lawrence G. Fess
Attorney, Agent, or Firm—Conrad O. Gardner; B. A. Donahue

[57] ABSTRACT

An ultrasonic scanning system utilizing a selectively rotatable reflector permitting selective use of multiple transducers mounted around the periphery of a water jet for flaw detection in composite materials.

4 Claims, 2 Drawing Sheets

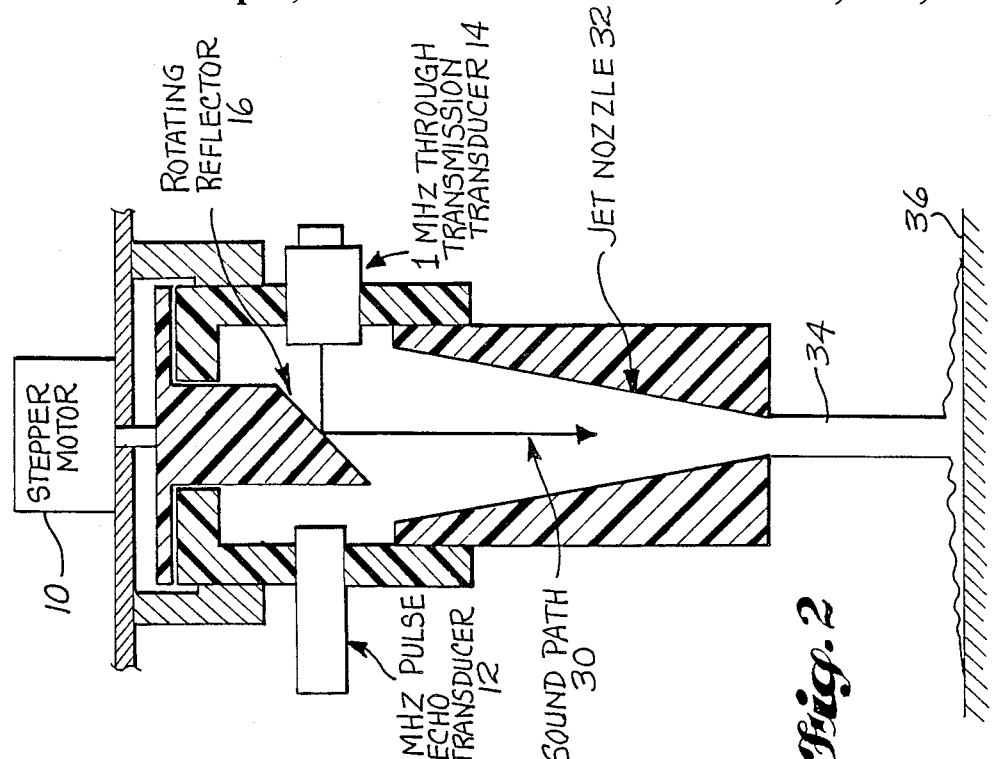
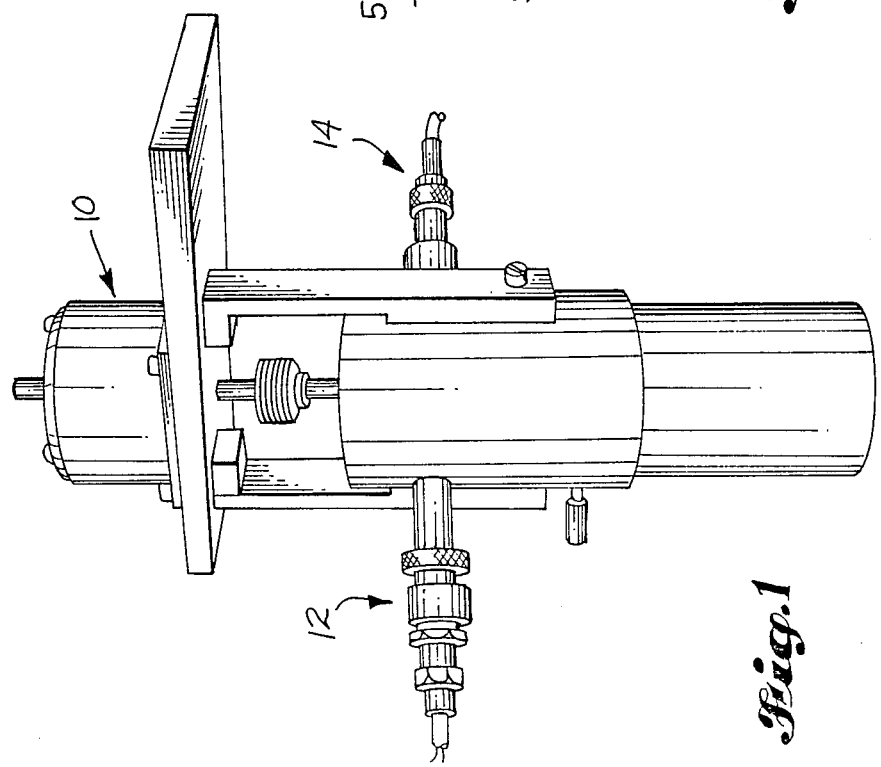
Fig. 2
Fig. 1

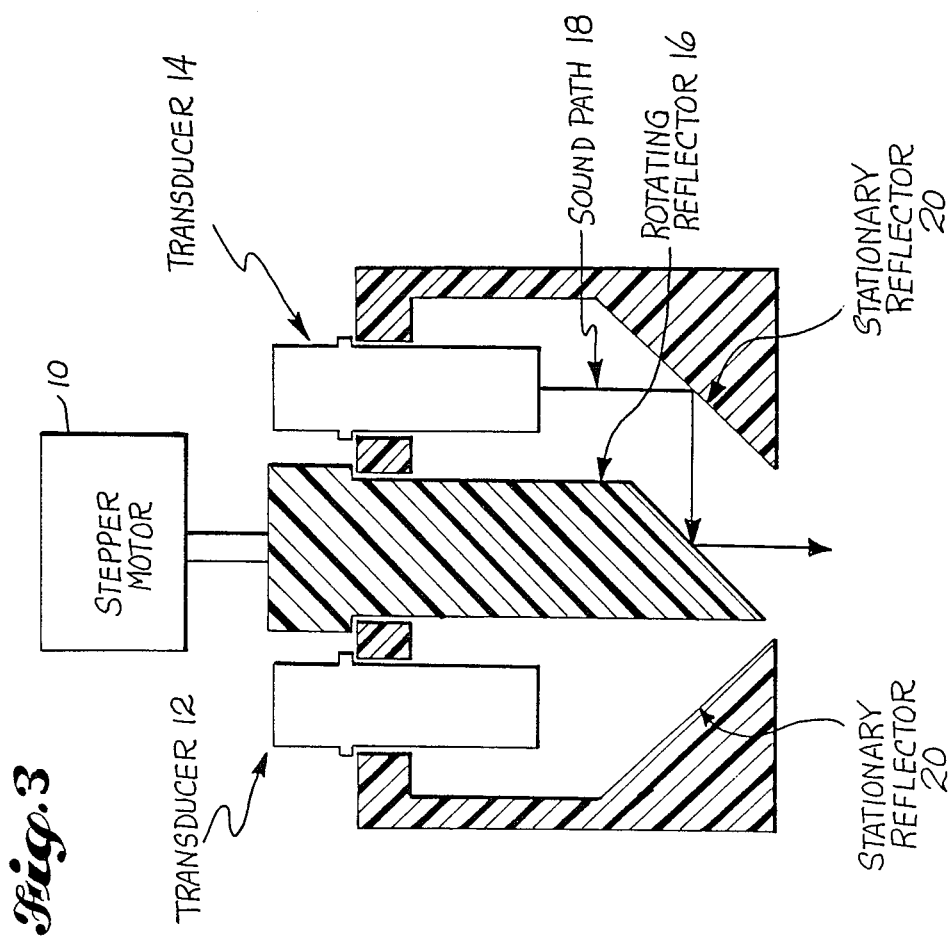

MULTIPLE ULTRASONIC TRANSDUCER WITH REMOTE SELECTOR

TECHNICAL FIELD

This invention relates to ultrasonic inspection, and more particularly, to a system and method of switching between different transducers while checking for flaws in composite materials with an ultrasonic scanning system.

BACKGROUND OF THE INVENTION

Ultrasonic testing is used for a variety of different applications from thickness measurements to flaw detection in aerospace and structural materials. The transducers used for these tests must be selected carefully to obtain the required spatial resolution and penetration. Damping, frequency, and focal properties required for a specific test often require the use of separate transducers. Transducers have heretofore been changed manually in order to obtain the characteristics desired for different tests. This is a time-consuming operation, particularly for multichannel testing and rapid inspection of large test pieces.

Since ultrasound is strongly reflected at air/solid or air/liquid interfaces, test pieces are often immersed in water or streams of water supplied by jets or bubblers to provide the coupling medium.

Various scanning techniques to provide pulsed laser radiation beams on a unitary path are exemplified in the prior art, for example U.S. Pat. No. 3,924,937.

Use of rotatable reflecting mirrors for light beams are known in the prior art as shown for example in U.S. Pat. No. 3,475,552.

Reflector means for reflecting ultrasonic energy from a plurality of transducers is known in the prior art from U.S. Pat. No. 3,107,521.

SUMMARY OF THE INVENTION

In accordance with preferred embodiments of the present invention, separate ultrasonic transducers are mounted around a rotating element. The end of the rotating element acts as a reflector that redirects the ultrasound from a transducer toward the inspection surface. A stepper motor coupled to the rotator permits selection of the transducer.

It is accordingly an object of the present invention to provide an ultrasonic scanning system which may be used with either immersion, bubbler, or water jet coupling of ultrasound to provide switching between different test modes of operation.

BRIEF DESCRIPTION OF THE DRAWINGS

These and other features of the present invention are more fully set forth below in the detailed description of the preferred embodiments and in the accompanying figures of which:

FIG. 1 is illustrative of a perspective view of the present multiple ultrasonic transducer with remote selector shown in cross sectional views in FIGS. 2 and 3;

FIG. 2 is a cross sectional view of the multiple ultrasonic transducer with remote selector shown in FIG. 1 wherein the axis of the transducers are normal to the central axis of the water jet; and, FIG. 3 is a cross sectional view of the multiple ultrasonic transducer with remote sensor shown in perspective in FIG. 1, however incorporating longitudinally disposed transducers with respect to the central axis of the system as may be used for immersion testing.

DETAILED DESCRIPTION OF THE INVENTION

A preferred embodiment of the present invention is shown in cross section in FIG. 2 wherein first and second ultrasonic transducers 12 and 14 are shown mounted around the periphery of and extending radially from the water jet traveling along the central axis with a sound path 30 of the present multiple ultrasonic transducer. Rotating reflector element 16 is coaxially disposed about the central axis and sound path diagrammed at 30. The end surface of rotating reflector 16 reflects and redirects the ultrasound from transducers 12 and 14 along the principal axis of the water jet which includes sound path 30. Stepper motor 10 is coupled to rotating reflector 16 and permits remote selection of whichever transducer 12 or 14 is to be activated. The apparatus of FIG. 2 comprising the first embodiment of the present invention utilizes a highly damped 5 MHz transducer 12 extending radially from the central axis, of the apparatus of FIG. 2 and is utilized for inspection of graphite composite laminates. Such pulse-echo inspection is effective for detection of certain foreign materials that may be inadvertently included in composite structures. Second transducer 14 also radially extending from the central axis of the apparatus of FIG. 2 comprises an undamped 1 MHz element utilized for through-transmission inspection over an extended dynamic range. Such transducer 14 is effective in the testing of thick honeycomb structures as well as metal bond components. Utilizing a water jet 34 exiting from jet nozzle 32 to transmit sound path 30 to a test piece 36, tests were conducted utilizing either pulse-echo transducer 12 activation or through-transmission testing utilizing transducer 14. Alternately, by switching the rotating reflector 16 between transducers 12 and 14 through stepper motor 10, a dual mode test was conducted to acquire both types of data during a single testing procedure. In the latter dual mode testing, through-transmission data was collected while the jet 34 was moving along the scan lines away from the scan start point. At the end of the initial scan line rotating reflector 16 was automatically switched and pulse-echo data was collected as the jet moved towards the start point on test piece 36. Upon returning to the start point, rotating reflector 16 was again moved to cause through-transmission transducer 14 to be active. After returning to the scan start point, the jet was indexed laterally and the cycle resumed until the area of interest on test piece 36 had been scanned.

For the test conducted with the two transducer jet, it was possible to have both the pulse-echo and through-transmission electronics (not shown) active simultaneously. The curved rear surface of the support for the reflector prevents sound from reaching the transducer that is active at a given time. In other words, the through-transmission transducer 14 can be active in generating high level 1 MHz sound pulses and not interfere with the 5 MHz pulse-echo tests conducted at the same time.

While only first and second transducers 12 and 14 were utilized in the apparatus of FIG. 2, several transducers may be arranged radially around the central axis of the jet 34. In such a case, a programmable stepper controller would select the appropriate transducer element for scanning each portion of a complex structure.

Turning now to FIG. 3 it may be observed that first and second transducers 12 and 14 have their axes parallel to the central axis of the apparatus shown in FIG. 3 as might be utilized for immersion testing. A stationary reflector 20 is associated with each of transducers 12 and 14 in the apparatus of FIG. 3 with the rotary reflector 16 selecting the active transducer.

What is claimed is:

1. An ultrasonic scanning system comprising:
   a plurality of ultrasonic wave emitting transducers circumferentially disposed about the central axis of said ultrasonic scanning system;
   a rotatable reflector coaxially disposed about said central axis of said ultrasonic scanning system;
   means coupled to said rotatable reflector for selectively rotating said rotatable reflector about said central axis of said ultrasonic scanning system to redirect ultrasonic from a selected one of said plurality of ultrasonic wave emitting transducers along said central axis of said ultrasonic scanning system; and,
   wherein said plurality of ultrasonic wave emitting transducers includes a first 5 MHz ultrasonic wave emitting transducer for pulse-echo inspection of graphite composite laminates, and a second 1 MHz ultrasonic wave emitting transducer for through-transmission inspection over an extended dynamic range.

2. The system according to claim 1 wherein said second 1 MHz ultrasonic wave emitting transducer has associated therewith a rotating reflector.

3. The system according to claim 2 wherein said second 1 MHz ultrasonic wave emitting transducer has associated therewith a stationary reflector.

4. The system according to claim 1 wherein said first 5 MHz ultrasonic wave emitting transducer has associated therewith a stationary reflector and said first 5 MHz ultrasonic wave emitting transducer has a longitudinal axis disposed parallel with said central axis of said ultrasonic scanning system.

* * * * *